United States Patent
Henderson

(10) Patent No.: US 11,242,132 B2
(45) Date of Patent: Feb. 8, 2022

(54) ENVIRONMENT SPECIFIC INPUT PROTECTION

(71) Applicant: GE Aviation Systems Limited, Cheltenham (GB)

(72) Inventor: George R. Henderson, Cheltenham (GB)

(73) Assignee: GE AVIATION SYSTEMS LIMITED

( * ) Notice: Subject to any disclaimer, the term of this patent is extended or adjusted under 35 U.S.C. 154(b) by 0 days.

(21) Appl. No.: 16/014,659

(22) Filed: Jun. 21, 2018

(65) Prior Publication Data

US 2019/0023377 A1 Jan. 24, 2019

(30) Foreign Application Priority Data

Jul. 24, 2017 (GB) .................................... 1711883

(51) Int. Cl.
| | |
|---|---|
| *B64C 13/16* | (2006.01) |
| *G05D 1/00* | (2006.01) |
| *A61B 5/16* | (2006.01) |
| *A61B 5/021* | (2006.01) |
| *A61B 5/024* | (2006.01) |
| *B64C 13/50* | (2006.01) |
| *B64D 45/04* | (2006.01) |

(52) U.S. Cl.
CPC .............. *B64C 13/16* (2013.01); *A61B 5/021* (2013.01); *A61B 5/024* (2013.01); *A61B 5/163* (2017.08); *B64C 13/506* (2018.01); *B64D 45/04* (2013.01); *G05D 1/0055* (2013.01)

(58) Field of Classification Search
None
See application file for complete search history.

(56) References Cited

U.S. PATENT DOCUMENTS 3,633,851 A * 1/1972 Marte ..................... B64C 13/12
                                                            244/229
8,892,274 B2   11/2014 Baudry
9,196,043 B2   11/2015 Pirim
9,218,002 B2   12/2015 Schulte et al.
(Continued)

FOREIGN PATENT DOCUMENTS

JP          2016/196285 A       11/2016

OTHER PUBLICATIONS

Great Britain Search and Examination Corresponding to GB17118837 dated Jan. 18, 2018.

*Primary Examiner* — Yuen Wong
*Assistant Examiner* — Hongye Liang
(74) *Attorney, Agent, or Firm* — Dority & Manning, P.A.

(57) ABSTRACT

One example aspect of the present disclosure relates to a method for assessing input. The method can include determining a state of the aerial vehicle. The method can include obtaining data indicative of an expected operator input based on the determined state. The method can include obtaining data indicative of an actual operator input. The method can include determining a state of operator behavior based on the expected operator input and the actual operator input. The method can include determining a control action for the aerial vehicle based on the determined state of the aerial vehicle and the determined state of the operator behavior. The method can include implementing the control action.

17 Claims, 9 Drawing Sheets

(56) References Cited

U.S. PATENT DOCUMENTS

| | | |
|---|---|---|
| 9,741,252 B2 | 8/2017 | Mere et al. |
| 10,308,370 B2 * | 6/2019 | Hinks .................... B64D 43/02 |
| 2012/0212353 A1 * | 8/2012 | Fung .................... B60W 30/08 |
| | | 340/905 |
| 2012/0330869 A1 | 12/2012 | Durham |
| 2013/0323688 A1 | 12/2013 | Whitlow et al. |
| 2014/0095416 A1 | 4/2014 | Butte et al. |
| 2015/0206000 A1 | 7/2015 | el Kaliouby et al. |
| 2016/0078365 A1 | 3/2016 | Baumard |
| 2016/0090097 A1 | 3/2016 | Grube et al. |
| 2018/0194349 A1 * | 7/2018 | McGill, Jr. ....... B60W 60/0013 |

* cited by examiner

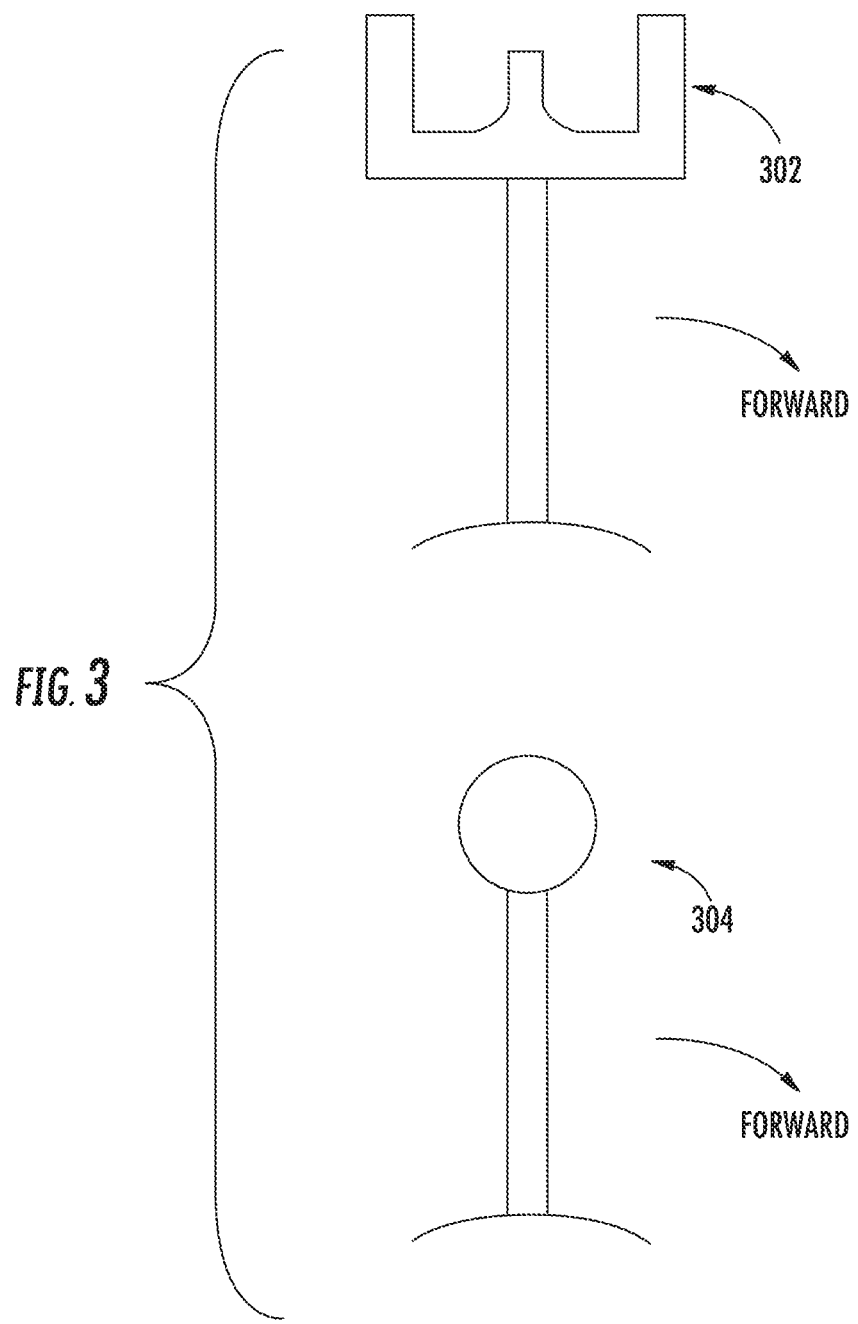

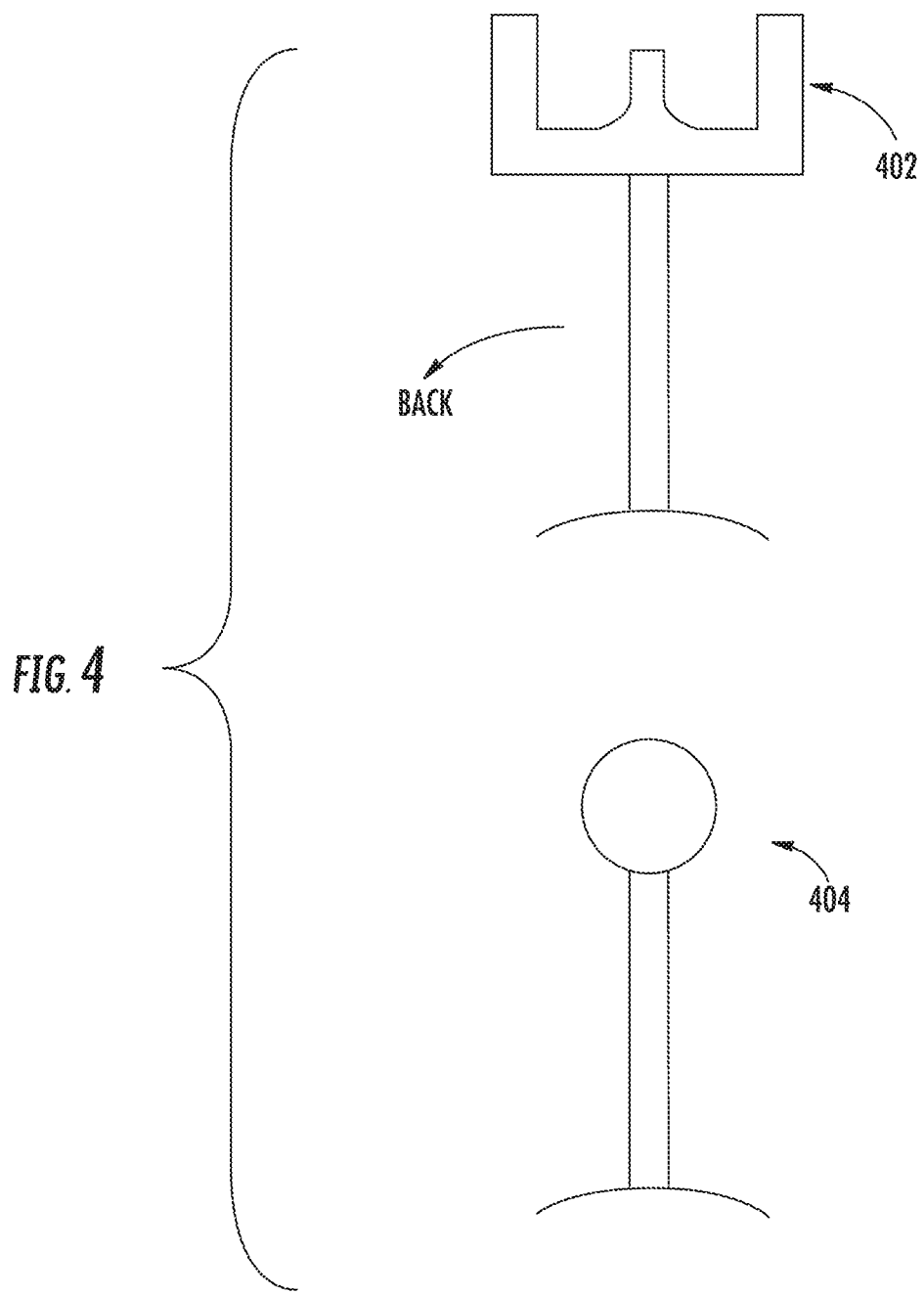

ENVIRONMENT SPECIFIC INPUT PROTECTION

FIELD

The present subject matter relates generally to aerial vehicles.

BACKGROUND

In the past, aerial vehicles have crashed because of pilot error. Sometimes the pilot error is caused by input that varies greatly from the input one would expect. For example, if an aerial vehicle is descending rapidly as the aerial vehicle is approaching a mountain range, then an accident can happen. However, at times, pilots have avoided an accident by operating outside of the norm. For example, landing an aerial vehicle in an unusual location be considered abnormal under normal circumstances. However, if all of the aerial vehicle's engines have been damaged due to bird strikes and the aerial vehicle cannot make it to an airport, then landing an aerial vehicle in an unusual location may be the best option.

BRIEF DESCRIPTION

Aspects and advantages of embodiments of the present disclosure will be set forth in part in the following description, or may be learned from the description, or may be learned through practice of the embodiments.

One example aspect of the present disclosure is directed to a system for assessing input. The system includes a memory device. The system includes one or more processors. The one or more processors are configured to determine a state of a vehicle. The one or more processors are configured to obtain data indicative of an expected operator input based on the determined state. The one or more processors are configured to obtain data indicative of an actual operator input. The one or more processors are configured to determine a state of operator behavior based on the expected operator input and the actual operator input. The one or more processors are configured to determine a control action for the aerial vehicle based on the determined state of the aerial vehicle and the determined state of the operator behavior. The one or more processors are configured to implement the control action.

Another example aspect of the present disclosure is directed to a method for assessing input. The method includes determining, by one or more computing devices, a state of a vehicle. The method includes obtaining, by the one or more computing devices, data indicative of an expected operator input based on the determined state. The method includes obtaining, by the one or more computing devices, data indicative of an actual operator input. The method includes determining, by the one or more computing devices, a state of operator behavior based on the expected operator input and the actual operator input. The method includes determining, by the one or more computing devices, a control action for the aerial vehicle based on the determined state of the aerial vehicle and the determined state of the operator behavior. The method includes implementing, by the one or more computing devices, the control action.

Other example aspects of the present disclosure are directed to systems, methods, aerial vehicles, avionics systems, devices, non-transitory computer-readable media for assessing input. Variations and modifications can be made to these example aspects of the present disclosure.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE DRAWINGS

Detailed discussion of embodiments directed to one of ordinary skill in the art are set forth in the specification, which makes reference to the appended figures, in which:

FIG. 3 depicts diagrams of normal operator behavior according to example embodiments of the present disclosure;

FIG. 4 depicts diagrams of abnormal operator behavior according to example embodiments of the present disclosure;

DETAILED DESCRIPTION

Figure 1:
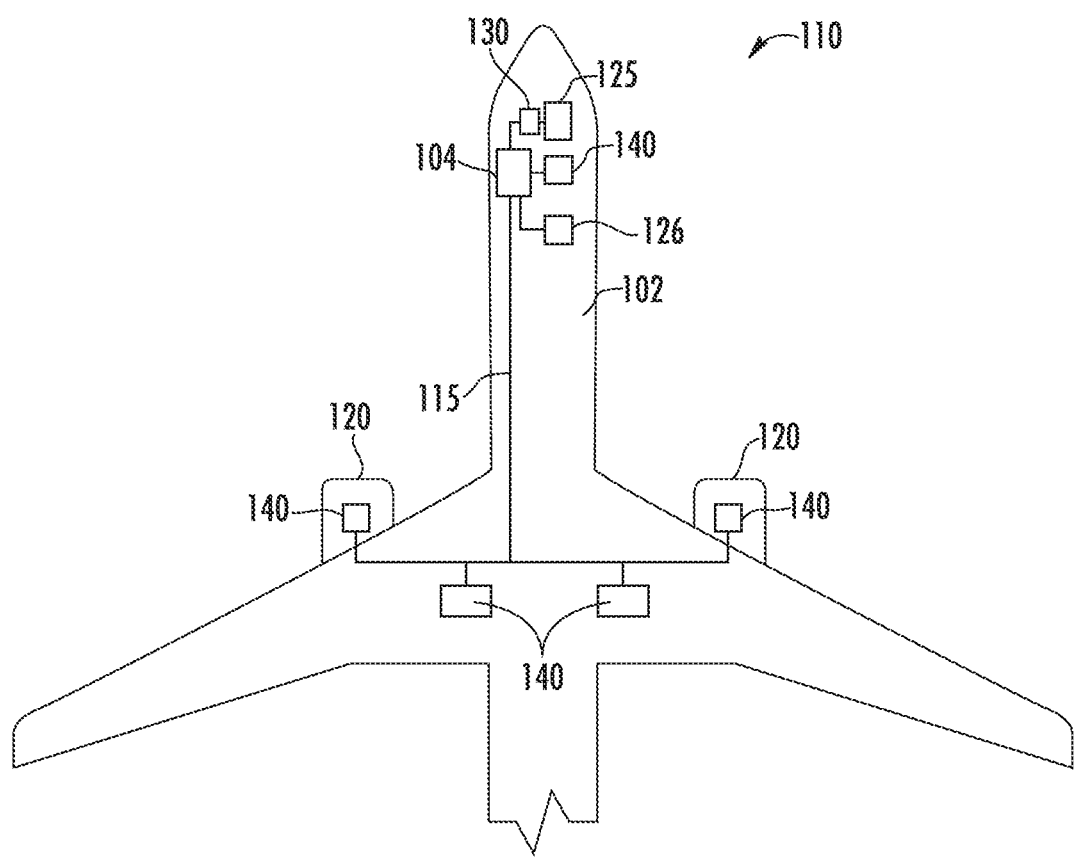
FIG. 1 depicts an aerial vehicle according to example embodiments of the present disclosure.

Reference now will be made in detail to embodiments, one or more examples of which are illustrated in the drawings. Each example is provided by way of explanation of the embodiments, not limitation of the embodiments. In fact, it will be apparent to those skilled in the art that various modifications and variations can be made in the present disclosure without departing from the scope or spirit of the invention. For instance, features illustrated or described as part of one embodiment can be used with another embodiment to yield a still further embodiment. Thus, it is intended that the present disclosure covers such modifications and variations as come within the scope of the appended claims and their equivalents.

As used in the specification and the appended claims, the singular forms "a," "an," and "the" include plural referents unless the context clearly dictates otherwise. The use of the term "about" in conjunction with a numerical value refers to within 25% of the stated amount.

An aerial vehicle can generate signals indicative of a state of the aerial vehicle. For example, signals indicative of the state of the aerial vehicle can include an air speed of the aerial vehicle. A state of the aerial vehicle can be determined based on the one or more signals. For example, the one or more signals can indicate that the aerial vehicle is stalling. As another example, the one or more signals can indicate that the aerial vehicle is performing normally.

One or more expected parameters can be retrieved based on the determined state of the aerial vehicle. For example, if the state of the aerial vehicle is a stalled state, then one or more expected parameters associated with a stalled aerial vehicle can be retrieved. As another example, if the state of the aerial vehicle is a normal state, then one or more expected parameters associated with a normal aerial vehicle can be retrieved. The one or more expected parameters can include passively observed parameters and/or deliberately inputted parameters.

One or more actual parameters can be received based on user input. The one or more actual parameters can include passively observed parameters. For example, one or more actions of the operator can be received. The one or more actual parameters can include deliberately inputted parameters. For example, positions of levers or other input devices can be received. The set of expected parameters can be compared with the set of actual parameters. For example, a task associated with an expected control of the aerial vehicle can indicate an expected operator eye contact with a display between 2 to 4 seconds; the actual time that the operator makes eye contact with the display can be compared with the expected time. As another example, an altitude of the aerial vehicle and a speed of the aerial vehicle can indicate that a thrust lever should be moved backwards; the actual position of the thrust lever can be compared with the expected movement (e.g., backwards).

A state of the input can be determined based on the comparison. For example, if the actual eye contact with the display is within the expected range, then the state of the input can be determined to be normal. As another example, if the actual eye contact with the display is outside of the expected range, then the state of the input can be determined to be abnormal. In another example, if the actual movement of the thrust lever is backwards and the expected movement of the thrust lever is backwards, then the state of the input can be determined to be normal. As another example, if the actual movement of the thrust lever is forwards and the expected movement of the thrust lever is backwards, then the state of the input can be determined to be abnormal. When the state of the input is determined to be abnormal, the aerial vehicle can be caused to initiate a protection mode. During the protection mode, the aerial vehicle can enter an automatic flight setting and become unresponsive or limitedly responsive to user input. An operating envelope can be a set of rules under which an operator can operate. In an embodiment, during protection mode, the operating envelope can tighten.

In this way, the systems and methods according to example aspects of the present disclosure can have a number of technical effects and benefits. For instance, example aspects of the present disclosure can have a technical effect of protecting an aerial vehicle from abnormal input of an operator (e.g., pilot) of the aerial vehicle.

In some embodiments, the systems and methods of the present disclosure also provide an improvement to a computing system in an aerial vehicle, such as the systems and methods for assessing input. For example, the systems and methods can determine a state of the aerial vehicle; obtain data indicative of an expected operator input based on the determined state; obtain data indicative of an actual operator input; determine a state of operator behavior based on the expected operator input and the actual operator input; determine a control action for the aerial vehicle based on the determined state of the aerial vehicle and the determined state of the operator behavior; and implement the control action. This can protect the computing system from processing harmful input.

As used herein, control polarity can mean engagement of an input device in a direction and/or a setting. For example, an incorrect control polarity can be a movement of a lever in a direction which is unexpected for a current set of circumstances. More specifically, an incorrect control polarity can be a movement of a thrust lever backwards when a movement of the thrust lever forwards is the only expected control polarity of the thrust lever. As used herein, control selection can mean engagement of a particular input device. For example, an incorrect control selection can be engagement of an input to control a first component, when control of a second component is expected. More specifically, an incorrect control selection can be a selection of a kill-switch for a left engine when a right engine is on fire. As used herein, control decision can mean a choice in light of an expected decision methodology. For example, an incorrect control decision can be a selection of an airport which does not have a runway long enough to accommodate the aerial vehicle, due to failing to consider a runway length required for the aerial vehicle and/or failing to consider a runway length of the selected airport as part of the decision methodology of the operator. As used herein, control timing can mean engagement of an input device in light of other aerial vehicle circumstances. For example, an incorrect control timing can be failing to respond to a control instruction issued to the operator of the aerial vehicle within an expected time frame. As used herein, missing controls can mean an absence of expected controls. For example, a set of words indicative of the operator checking cabin pressure whilst climbing through 10,000 ft. can be expected, and if absent, can be a missing control. As used herein, an operating envelope can be a set of rules under which an operator can operate. As used herein, broadening the operating envelope means that the set of rules under which the operator can operate are relaxed or loosened. As used herein, tightening the operating envelope means adding limits to the set of rules under which the operator can operate.

FIG. 1 depicts an example system for assessing input according to example embodiments of the present disclosure. As shown, the system can include an aerial vehicle 102. The aerial vehicle 102 can include an onboard computing system 110. As shown in FIG. 1, the onboard computing system 110 can include one or more onboard computing device(s) 104 that can be associated with, for instance, an avionics system. The onboard computing device(s) 104 can be coupled to a variety of systems on the aerial vehicle 102 over a communications network 115. The communications network 115 can include a data bus or combination of wired and/or wireless communication links.

The onboard computing device(s) 104 can be in communication with a display system 125 including one or more display device(s) that can be configured to display or otherwise provide information generated or received by the system 110 to flight crew members of the aerial vehicle 102. The display system 125 can include a primary flight display, a multipurpose control display unit, or other suitable flight displays commonly included within a cockpit of the aerial vehicle 102.

The onboard computing devices(s) 104 can also include and/or be in communication with a crew sensing system 126. The crew sensing system 126 can include one or more sensors to sense the actions and/or state of flight crew members through different modalities including, among other things, speech, eye tracking, physiological condition, and/or control positions. The one or more sensors can include one or more cameras, microphones, etc. The crew sensing system 126 can include and/or be associated with, any suitable number of individual microprocessors, power supplies, storage devices, interface cards, and other standard components.

The onboard computing device(s) 104 can also be in communication with a flight control computer 130. The flight control computer 130 can, among other things, automate the tasks of piloting and tracking the flight plan of the aerial vehicle 102. The flight control computer 130 can include or be associated with, any suitable number of individual microprocessors, power supplies, storage devices, interface cards, auto flight systems, flight management computers, and other standard components. The flight control computer 130 can include or cooperate with any number of software programs (e.g., flight management programs) or instructions designed to carry out the various methods, process tasks, calculations, and control/display functions necessary for operation of the aerial vehicle 102. The flight control computer 130 is illustrated as being separate from the onboard computing device(s) 104. Those of ordinary skill in the art, using the disclosures provided herein, will understand that the flight control computer 130 can also be included with or implemented by the onboard computing device(s) 104.

The onboard computing device(s) 104 can also be in communication with one or more aerial vehicle control system(s) 140. The aerial vehicle control system(s) 140 can be configured to perform various aerial vehicle operations and control various settings and parameters associated with the aerial vehicle 102. For instance, the aerial vehicle control system(s) 140 can be associated with one or more engine(s) 120 and/or other components of the aerial vehicle 102. The aerial vehicle control system(s) 140 can include, for instance, digital control systems, throttle systems, inertial reference systems, flight instrument systems, engine control systems, auxiliary power systems, fuel monitoring systems, engine vibration monitoring systems, communications systems, flap control systems, flight data acquisition systems, and other systems.

Any or all of the onboard computing system 110, the onboard computing device(s) 104, the flight control computer, and the aerial vehicle control system(s) 140 can include and/or be in communication with input devices. According to example aspects of the present disclosure, a state of the aerial vehicle can be determined and the input devices can be limited based on the state, as described in further detail in reference to FIG. 6 and FIG. 7 below.

The numbers, locations, and/or orientations of the components of example aerial vehicle 102 are for purposes of illustration and discussion and are not intended to be limiting. Those of ordinary skill in the art, using the disclosures provided herein, shall understand that the numbers, locations, and/or orientations of the components of the aerial vehicle 102 can be adjusted without deviating from the scope of the present disclosure.

Figure 2A:
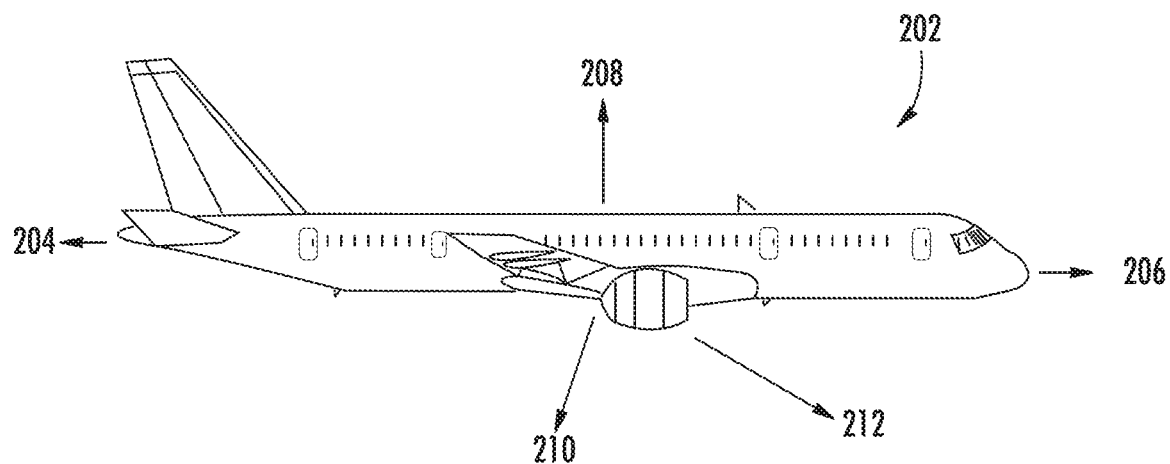
FIG. 2A depicts a diagram of a state of an aerial vehicle according to example embodiments of the present disclosure.
Figure 2B:
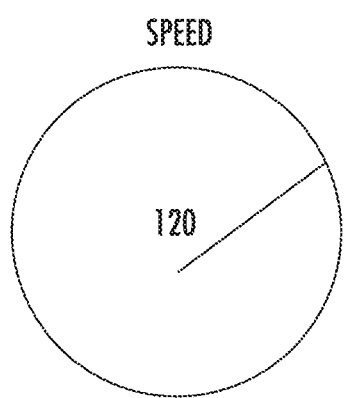
FIG. 2B depicts a display of an aerial vehicle according to example embodiments of the present disclosure.
Figure 2C:
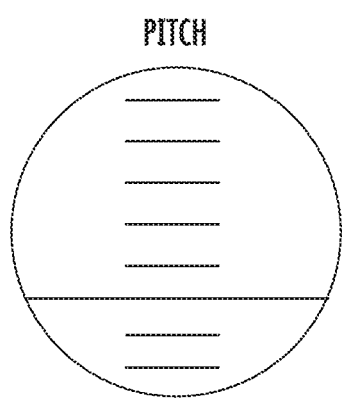
FIG. 2C depicts a display of an aerial vehicle according to example embodiments of the present disclosure.

FIG. 2A depicts a diagram to example embodiments of the present disclosure. A state of an aerial vehicle 202, in this case a stalling of the aerial vehicle 202, is shown. The variety of detected forces can indicate that the aerial vehicle 202 is in a stalled state. For example, a drag force 204, a lift force 208, a weight of the aerial vehicle force 210, and a thrust force 206 can be considered. A total movement 212 of the aerial vehicle 202 in view of the forces can indicate that the aerial vehicle 202 is in a stalled state. FIG. 2B depicts an example embodiment of an output display associated with a speed. FIG. 2C depicts an example embodiment of an output display associated with a pitch. The state of the aerial vehicle can be determined by values associated with a control system. For example, the values shown in the output displays of FIGs. B and C can be values associated with a stalled state. The display system 125 can comprise the output displays of FIGs. B and C. Although FIGS. 2A-2C depict an aerial vehicle stalling, a number of aerial vehicle conditions can be detected. For example, one or more engine failures can be detected.

FIG. 3 illustrates normal and/or expected operator behavior according to example embodiments of the present disclosure. The normal and/or expected operator behavior can be based on the determined state of the aerial vehicle, in the case of FIGS. 2A-2C, a stalled state. For example, moving a yoke 302 forward can be an expected input and/or normal input. If the yoke 302 is moved forward, this expected behavior can be allowed. In an embodiment, the aerial vehicle 202 can automatically operate as if the yoke 302 is moved to an expected position for the current detected state. Additionally, moving a thrust lever 304 forward can be an expected input and/or normal input. If the thrust lever 304 is moved forward, this expected behavior can be allowed. In an embodiment, the aerial vehicle 202 can automatically operate as if the thrust lever 304 is moved to an expected position for the current detected state.

FIG. 4 illustrates abnormal and/or unexpected operator behavior according to example embodiments of the present disclosure. The abnormal and/or unexpected operator behavior can be based on the determined state of the aerial vehicle, in the case of FIGS. 2A-2C, a stalled state. For example, moving a yoke 402 backwards can be an unexpected input and/or abnormal input. If the yoke 402 is moved backwards, this expected behavior will not be allowed. As shown, there might be no restriction on the movement of a thrust lever 404.

Although FIGS. 2A, 2B, 2C, 3, and 4 depict detection of an incorrect control polarity (i.e., moving levers in an opposite of an expected direction), a number of other deliberately inputted errors can be detected. In an embodiment, an incorrect control selection can be detected. For example, a fire can be detected on a right engine and a signal from a left engine kill switch can be detected. In an embodiment, an incorrect control decision can be detected. For example, a signal to divert an aerial vehicle to an airport with a runway that is too short for the aerial vehicle to land can be detected. In an embodiment, an incorrect control timing can be detected. For example, a signal to deploy a landing gear while the aerial vehicle is travelling faster than a maximum gear extension speed can be detected. In an embodiment, missed controls can be detected. For example, an expected signal to check cabin pressure at 10,000 ft. can be detected as missing.

Although FIGS. 2A, 2B, 2C, 3, and 4 depict detection of incorrect deliberate input, incorrect passively observed input can also be detected. For example, an operator may have a checklist of items to go through in order to follow proper protocol for a particular task. One or more cameras can record the operator to detect if each item of the checklist is performed, is performed in a correct order, and is performed in an appropriate time range. As another example, a proper protocol can instruct co-operators to have a scripted dialog during another particular task. One or more microphones can record the co-operators to detect if the scripted dialog takes place. As a further example, proper protocol can dictate that eyes of an operator are fixed on a spot in a display for a particular time range. One or more cameras can record the eyes of the operator to detect if the eyes of the operator are fixed on the spot during the particular time range.

Figure 5:
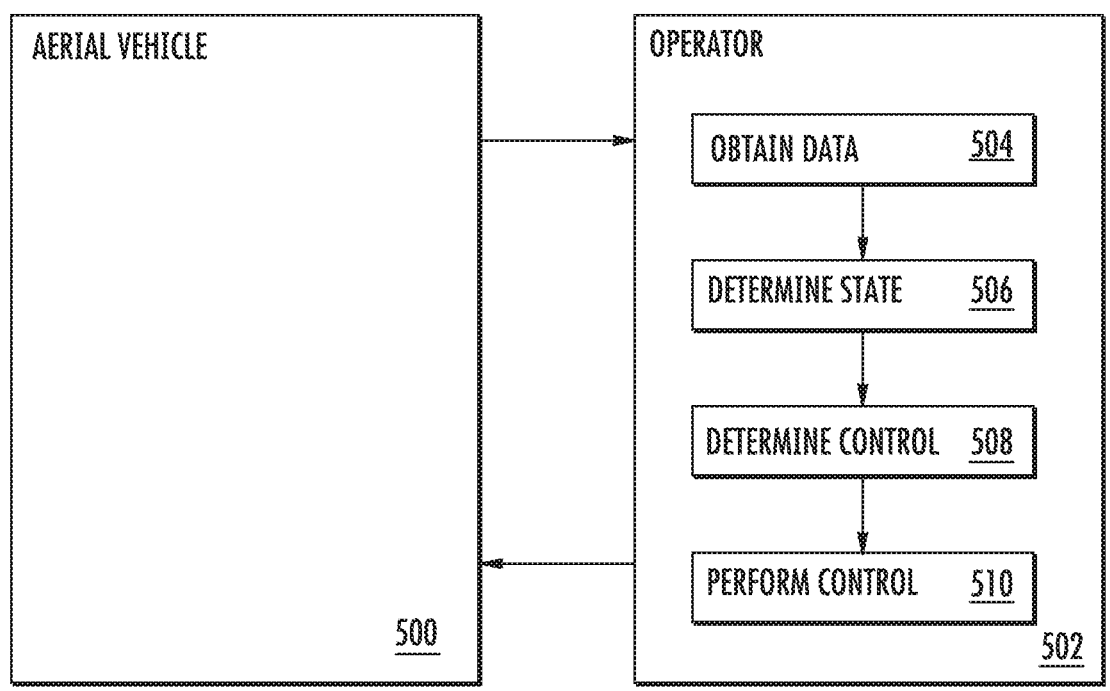
FIG. 5. depicts a flow diagram according to example embodiments of the present disclosure.

FIG. 5 depicts a flow diagram of an example method performed by an operator 502. FIG. 5 also depicts a relationship between an aerial vehicle 500 and the operator 502. At (504), the operator 502 obtains data from the aerial vehicle 500. Data can be obtained, for example, through visual output (e.g., an image on a display), auditory output (e.g., an auditory alert representing a state of the aerial vehicle 500), tactile output (e.g., a vibration representing a state of a component of the aerial vehicle), etc. At (506), the operator 502 can determine the state of the aerial vehicle 500. The state of the aerial vehicle 500 can be determined based on the obtained data. The operator 502 can provide an indication of the state of the aerial vehicle 500 vocally (e.g., radioing in the state of the aerial vehicle 500 to a ground system, discussing the state of the aerial vehicle 500 with a co-operator, telling the state of the aerial vehicle 500 to a flight crew, stating the state of the aerial vehicle 500 aloud to herself, etc.). The operator 502 can provide a signal indication of the state of the aerial vehicle 500 (e.g., broadcasting a Morse code signal, inputting text indicative of the state of the aerial vehicle 500, engaging an input device (for example, a button to indicate seat belts should be worn at this time), etc.).

At (508), the operator 502 can determine a control or action to take. The determined control can be based on the determined state. The operator 502 can provide an indication of the determined control vocally (e.g., radioing a ground system to advice the ground system of the determined control, discussing the determined control with a co-operator, telling the determined control to a flight crew, stating the determined control aloud to herself, etc.). The operator 502 can provide a signal indication of the determined control (e.g., inputting text indicative of the determined control, engaging an input device (for example, when the determined control involves changing a flight plan, a button to cycle through possible new locations can be engaged), etc.). At (510), the operator 502 can perform the control. The aerial vehicle 502 can respond to the performed control.

In an aspect, passively observed operator input can be assessed based on the method 500. For example, if the operator 502 is observed moving to (506) without spending a normal time range on (504) (for example, speaking the state of the aerial vehicle 500 without having eye contact with a display for an appropriate time range), then an abnormal operator behavior can be observed. Similarly, if the operator 502 is observed moving to (508) to quickly (for example, speaking a control to perform without speaking a state of the aerial vehicle 500), then an abnormal operator behavior can be observed. Similarly, if the operator 502 is observed moving to (510) to quickly (for example, engaging an input device without speaking a control to be performed), then an abnormal operator behavior can be observed. In an embodiment, if the operator 502 does not move to (510) when expected (for example, failing to act to recover a state of the aerial vehicle), then an abnormal operator behavior can be observed. In an embodiment, failure in multiple stages may be detected. For example, an incapacitated crew member can neither obtain data 504 nor perform control functions 510. This can be considered a failure of multiple stages and would be an abnormal behavior, which can be detected. In an embodiment, one observed abnormal operator action can cause a state of the operator behavior to change from normal to abnormal. In another embodiment, a threshold number of abnormal actions can be performed before the state of the operator behavior changes from normal to abnormal. In another embodiment, a threshold number of abnormal actions can be performed within a time period before the state of the operator behavior changes from normal to abnormal. In another embodiment, different abnormal actions can be weighted. For example, an observed abnormal behavior at (504) can be weighted more lightly than an observed abnormal behavior at (510). Under such an embodiment, a threshold weighted value of abnormal behaviors may occur (or occur within a certain time period) before the state of the operator behavior changes from normal to abnormal.

Figure 6:
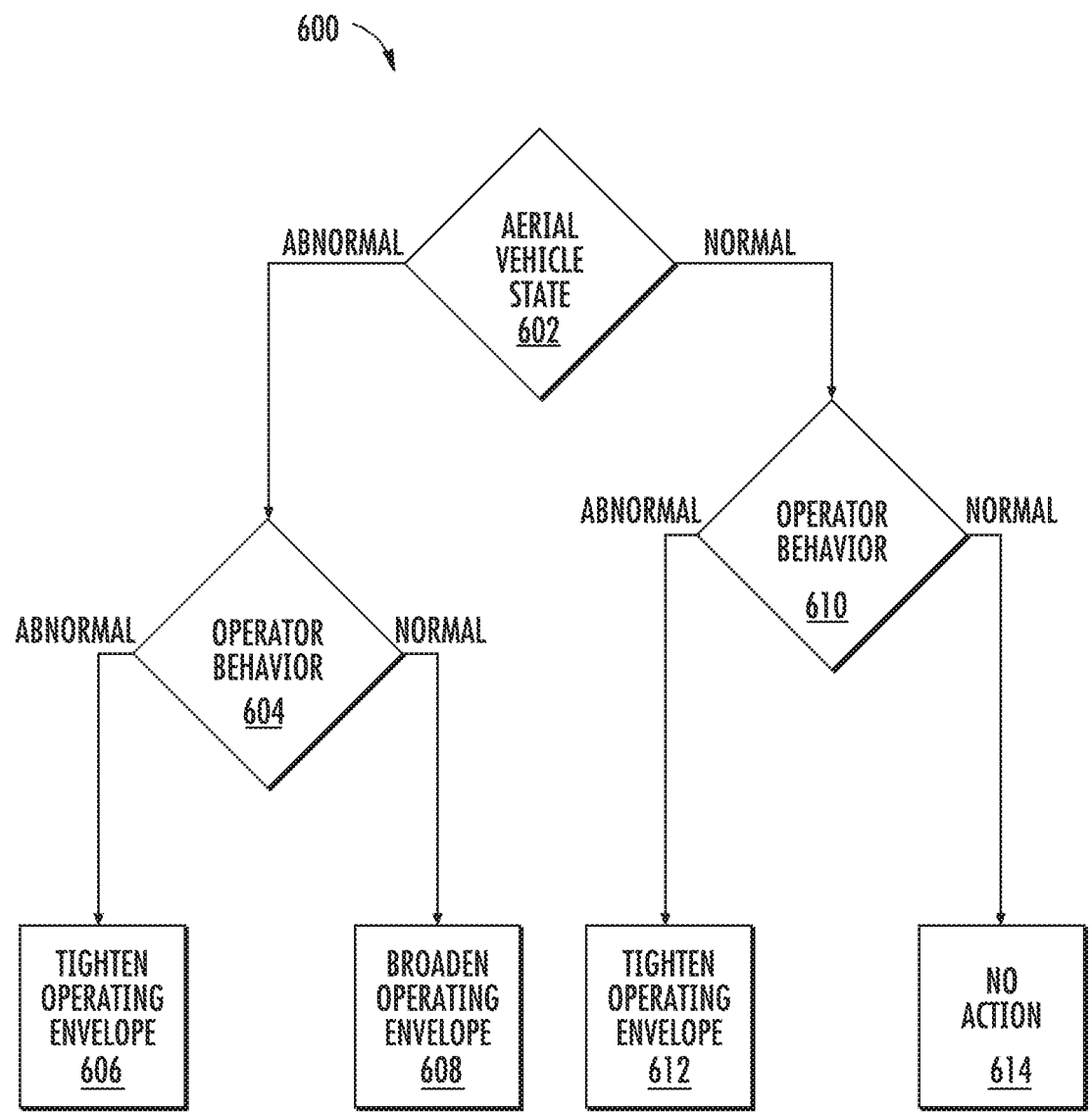
FIG. 6 depicts a flow diagram according to example embodiments of the present disclosure.

FIG. 6 depicts a flow diagram of an example method 600 for assessing input. The method of FIG. 6 can be implemented using, for instance, the one or more computing device(s) 802 and/or the one or more processor(s) 804 of the control system 800 of FIG. 8. FIG. 6 depicts steps performed in a particular order for purposes of illustration and discussion. Those of ordinary skill in the art, using the disclosures provided herein, will understand that various steps of any of the methods disclosed herein can be adapted, modified, rearranged, performed simultaneously, or modified in various ways without deviating from the scope of the present disclosure.

At (602), an aerial vehicle state can be determined. For example, the processor 804 can determine a state of the aerial vehicle. For example, the determined state of the aerial vehicle can be an abnormal state or a normal state. In an embodiment, a specific abnormal state can be determined. As an example, a specific abnormal state that can be determined is a stalled state. As another example, another specific abnormal state that can be determined is an engine fire. In an embodiment, when a state is determined to be normal, the method can move to (610). In an embodiment, specific normal state can be determined. As an example, a specific normal state that can be determined is a state associated with icy conditions. As another example, another specific normal state that can be determined is a state associated with approaching a mountain range.

When a state is determined to be abnormal, the method can move to (604). At (604), operator behavior can be compared with operator behavior expected for the determined state. For example, the processor 804 can compare operator behavior with operator behavior expected for the determined state. If the operator behavior deviates from an expected operator behavior, then the operator behavior can be abnormal. Operator behavior can include passively observed behavior and/or behavior associated with deliberately inputting control signals. Comparing operator behavior with expected operator behavior can include comparing an actual control polarity with an expected control polarity. Comparing operator behavior with expected operator behavior can include comparing an actual control selection with an expected control selection. Comparing operator behavior with expected operator behavior can include comparing an actual control decision with an expected control decision. Comparing operator behavior with expected operator behavior can include comparing an actual control timing with an expected control timing. Comparing operator behavior with expected operator behavior can include detecting that a control signal was not transmitted when expected. Comparing operator behavior with expected operator behavior can include comparing a time associated with eyes of an operator fixed on a display with an expected time. Comparing operator behavior with expected operator behavior can include comparing one or more words spoken with one or more expected words. Comparing operator behavior with expected operator behavior can include comparing a thought process of an operator with an expected thought process. Comparing operator behavior with expected operator behavior can include comparing a body language of an operator with an expected body language. Comparing operator behavior with expected operator behavior can include comparing a personality of an operator with an expected personality. In an embodiment, when the comparison of the operator behavior with the operator behavior expected for the determined state determines that the operator behavior is abnormal, then the method 600 can move to (606). In an embodiment, when the comparison of the operator behavior with the operator behavior expected for the determined state determines that the operator behavior is normal, then the method 600 can move to (608). An operating envelope can be a set of rules under which an operator can operate. The operating envelope can be determined by the state of the aerial vehicle and the state of the operator behavior.

At (606), the aerial vehicle is determined to be in an abnormal state and the operator behavior is determined to be abnormal. Under such circumstances, the operating envelope can be tightened. For example, low-level, rule-based protections can be added to the operating envelope. As a further example, an operator can be allowed to alter a pitch upwards of the aerial vehicle to maintain an airspeed but prevented from altering the pitch downwards. At (608), the aerial vehicle is determined to be in an abnormal state and the operator behavior is determined to be normal. Under such circumstances, the operating envelope can be broadened. For example, landing an aerial vehicle in an unusual location, such as a highway, a field, or a body of water, may normally be prohibited. However, if two engines of the aerial vehicle are inoperative, landing the aerial vehicle in the unusual location may be allowed.

At (610), operator behavior can be compared with operator behavior expected for the determined state. For example, the processor 804 can compare operator behavior with operator behavior expected for the determined state. If the operator behavior deviates from an expected operator behavior, then the operator behavior can be abnormal. Comparing operator behavior with expected operator behavior can include comparing an actual control polarity with an expected control polarity. Comparing operator behavior with expected operator behavior can include comparing an actual control selection with an expected control selection. Comparing operator behavior with expected operator behavior can include comparing an actual control decision with an expected control decision. Comparing operator behavior with expected operator behavior can include comparing an actual control timing with an expected control timing. Comparing operator behavior with expected operator behavior can include detecting that a control signal was not transmitted when expected. Comparing operator behavior with expected operator behavior can include comparing a time associated with eyes of an operator fixed on a display with an expected time. Comparing operator behavior with expected operator behavior can include comparing one or more words spoken with one or more expected words. Comparing operator behavior with expected operator behavior can include comparing a thought process of an operator with an expected thought process. Comparing operator behavior with expected operator behavior can include comparing a body language of an operator with an expected body language. Comparing operator behavior with expected operator behavior can include comparing a personality of an operator with an expected personality. In an embodiment, when the comparison of the operator behavior with the operator behavior expected for the determined state determines that the operator behavior is abnormal, then the method 600 can move to (612). In an embodiment, when the comparison of the operator behavior with the operator behavior expected for the determined state determines that the operator behavior is normal, then the method 600 can move to (614).

At (612), the aerial vehicle is determined to be in a normal state and the operator behavior is determined to be abnormal. Under such circumstances, the operating envelope can be tightened. For example, a protection system can be added to the operating envelope. For example, the aerial vehicle can enter an automated mode and input from the operator can be ignored. At (614), the aerial vehicle is determined to be in a normal state and the operator behavior is determined to be normal. Under such circumstances, the aerial vehicle can take no action and input from the operator can be processed as normal.

Figure 7:
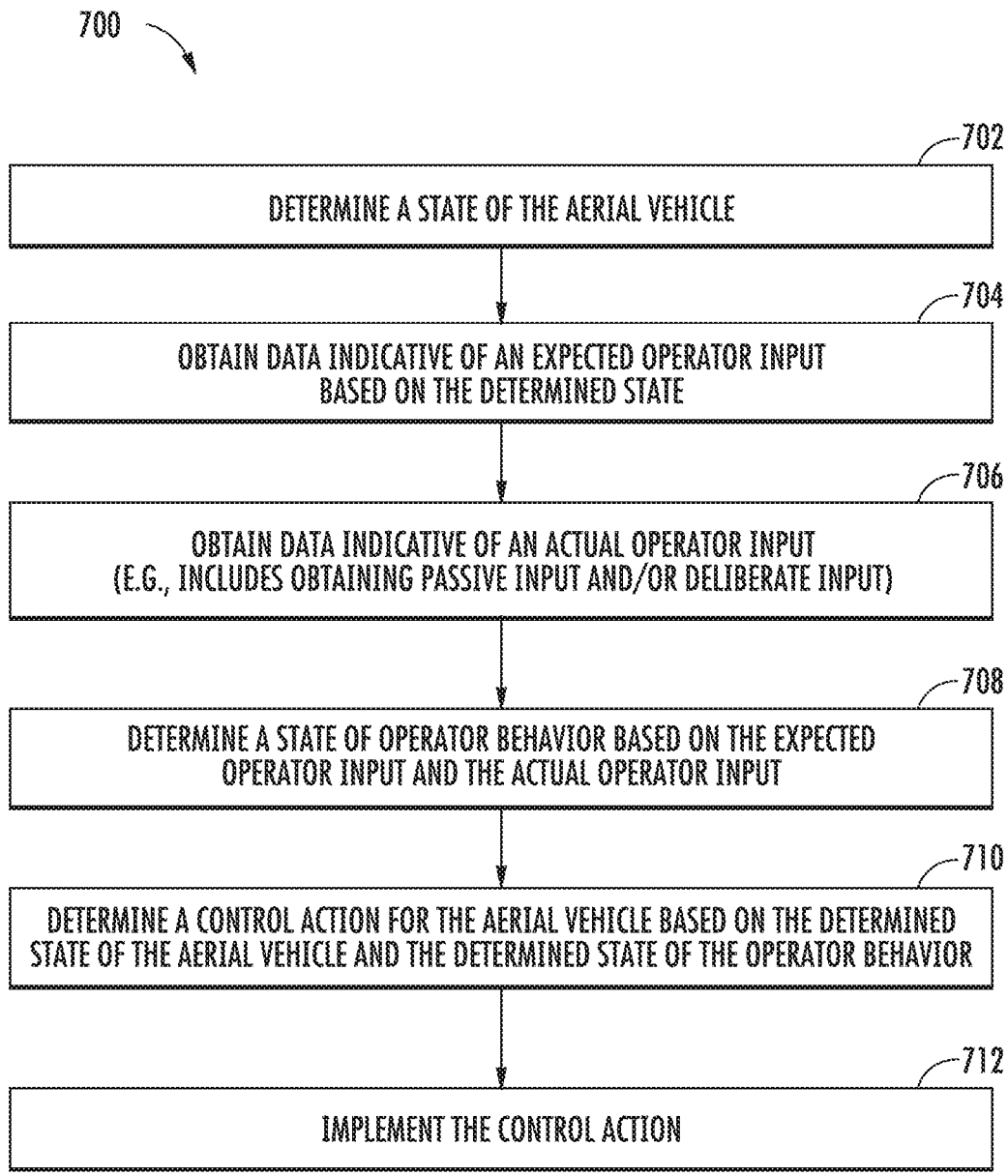
FIG. 7 depicts a flow diagram according to example embodiments of the present disclosure.

FIG. 7 depicts a flow diagram of an example method 700 for assessing input. The method of FIG. 7 can be implemented using, for instance, the one or more computing device(s) 802 and/or the one or more processor(s) 804 of the control system 800 of FIG. 8. FIG. 7 depicts steps performed in a particular order for purposes of illustration and discussion. Those of ordinary skill in the art, using the disclosures provided herein, will understand that various steps of any of the methods disclosed herein can be adapted, modified, rearranged, performed simultaneously, or modified in various ways without deviating from the scope of the present disclosure.

At (702), a state of the aerial vehicle can be determined. For example, the processor 804 can determine a state of the aerial vehicle. For instance, one or more signals indicative of performance of the aerial vehicle can be used to determine the state of the aerial vehicle. For example, one of more signals indicative of a plurality of forces can be used to determine if the aerial vehicle is in an abnormal state and/or a stalled state. In another instance, the absence of one or more signals from an engine can be used to determine an abnormal state and/or an engine failure state. In an aspect, the state of the aerial vehicle can be normal or abnormal. In another aspect, the state of the aerial vehicle can be more specific than normal and abnormal. For example, the state of the aerial vehicle can include a stall state, an engine failure state, etc.

At (704), data indicative of an expected operator input can be obtained based on the determined state. For example, the processor 804 can obtain data indicative of an expected operator input based on the determined state. Operator input can include passively observed input and/or deliberately inputting control signals. The expected operator input can include an expected control polarity. For example, the expected operator input can include a forward movement of a control, such as a yoke or a thrust lever. The expected operator input can include an expected control selection. For example, the expected operator input can include kill switch for an engine. The expected operator input can include an expected control decision. For example, the expected operator input can include a route to a new airport, wherein the new airport includes a runway long enough to accommodate the aerial vehicle. The expected operator input can include an expected control timing. For example, the expected operator input can include not receiving a signal to deploy a landing gear when the aerial vehicle is travelling faster than a maximum gear extension speed. The expected operator input can include an expected control signal. For example, the expected operator input can include an expected set of words indicative of the user checking cabin pressure whilst climbing through 10,000 ft. The expected operator input can include an expected time associated with eyes of an operator fixed on a display. The expected operator input can include one or more expected words. The expected operator input can include an expected thought process. The expected operator input can include an expected body language. The expected operator input can include an expected personality. The expected operator input can include an expected facial expression. The expected operator input can include an expected physical posture. The expected operator input can include an expected physiological condition. The expected operator input can include an expected inter-control movement.

At (706), data indicative of an actual operator input can be obtained. For example, the processor 804 can obtain data indicative of an actual operator input. Obtaining actual operator input can include obtaining deliberately inputting control signals. As in example, actual operator input can include signals indicative of a position and/or a change in position of an input device. In an aspect, the input device can include a yoke. In an aspect, the input device can include a thrust lever. Alternatively or additionally, obtaining actual operator input can include obtaining passively observed input. As an example, one or more cameras and/or one or more microphones can record data indicating a condition of the operator. The data indicating the condition can include operator speech, operator eye tracking, operator facial expressions, operator physical posture, operator inter-control movement, operator physiological conditions (e.g., heart rate, blood pressure, etc.), the like, and/or any combination of the foregoing.

At (708), a state of operator behavior can be determined based on the expected operator input and the actual operator input. For example, the processor 804 can determine a state of operator behavior based on the expected operator input and actual operator input. The state of operator behavior can be determined based on passively observed input and/or deliberately inputting control signals. Determining a state of operator behavior based on the expected operator input and the actual operator input can include comparing an actual control polarity with an expected control polarity. Determining a state of operator behavior based on the expected operator input and the actual operator input can include comparing an actual control selection with an expected control selection. Determining a state of operator behavior based on the expected operator input and the actual operator input can include comparing an actual control decision with an expected control decision. Determining a state of operator behavior based on the expected operator input and the actual operator input can include comparing an actual control timing with an expected control timing. Determining a state of operator behavior based on the expected operator input and the actual operator input can include determining whether an expected control signal is present. Determining a state of operator behavior based on the expected operator input and the actual operator input can include comparing an observed time associated with eyes of an operator fixed on a display with an expected time associated with eyes of an operator fixed on the display. Determining a state of operator behavior based on the expected operator input and the actual operator input can include comparing one or more observed words with one or more expected words. Determining a state of operator behavior based on the expected operator input and the actual operator input can include comparing an observed thought process with an expected thought process. Determining a state of operator behavior based on the expected operator input and the actual operator input can include comparing an observed body language with an expected body language. Determining a state of operator behavior based on the expected operator input and the actual operator input can include comparing an observed personality with an expected personality. Determining a state of operator behavior based on the expected operator input and the actual operator input can include comparing an observed facial expression with an expected facial expression. Determining a state of operator behavior based on the expected operator input and the actual operator input can include comparing an observed physical posture with an expected physical posture. Determining a state of operator behavior based on the expected operator input and the actual operator input can include comparing an observed physiological condition with an expected physiological condition. Determining a state of operator behavior based on the expected operator input and the actual operator input can include comparing an observed inter-control movement with an expected inter-control movement.

At (710), a control action can be determined for the aerial vehicle based on the determined state of the aerial vehicle and the determined state of the operator behavior. For example, the processor 804 can determine a control action for the aerial vehicle based on the determined state of the aerial vehicle and the determined state of the operator behavior. An operating envelope can be a set of rules under which an operator can operate. The control action can broaden or tighten the operating envelope. When the aerial vehicle state is determined to be abnormal and the operator behavior state is determined to be abnormal, the control action can tighten the operating envelope. For example, tightening the operating envelope can include adding low-level, rule based protections. When the aerial vehicle state is determined to be abnormal and the operator behavior state is determined to be normal, the control action can broaden the operating envelope. For example, the rules under which an operator is allowed to operate can be loosened. When the aerial vehicle state is determined to be normal, when the operator behavior state is determined to be abnormal, the control action can tighten the operating envelope. For example, tightening the operating envelope can include triggering a protection system. When the aerial vehicle state is determined to be stalled, when the operator behavior state is determined to be abnormal, the control action can ignore a signal indicative of a backward movement of a yoke. At (712), the control action can be implemented. For example, the processor 804 can implement the control action.

Figure 8:
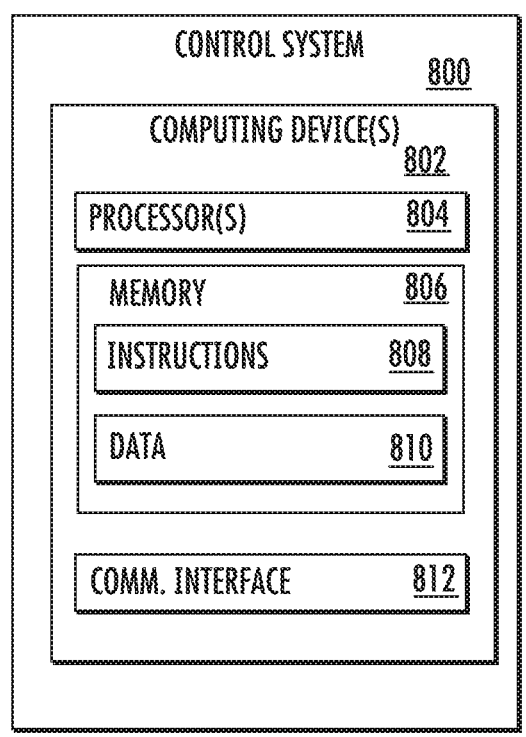
FIG. 8 depicts a control system for implementing one or more aspects according to example embodiments of the present disclosure.

FIG. 8 depicts a block diagram of an example control system 800 that can be used to implement methods and systems according to example embodiments of the present disclosure. The control system 800 can be any control device or system described with reference to FIG. 1. As shown, the control system 800 can include one or more computing device(s) 802. The one or more computing device(s) 802 can include one or more processor(s) 804 and one or more memory device(s) 806. The one or more processor(s) 804 can include any suitable processing device, such as a microprocessor, microcontroller, integrated circuit, logic device, or other suitable processing device. The one or more memory device(s) 806 can include one or more computer-readable media, including, but not limited to, non-transitory computer-readable media, RAM, ROM, hard drives, flash drives, or other memory devices.

The one or more memory device(s) 806 can store information accessible by the one or more processor(s) 804, including computer-readable instructions 808 that can be executed by the one or more processor(s) 804. The instructions 808 can be any set of instructions that when executed by the one or more processor(s) 804, cause the one or more processor(s) 804 to perform operations. The instructions 808 can be software written in any suitable programming language or can be implemented in hardware. In some embodiments, the instructions 808 can be executed by the one or more processor(s) 804 to cause the one or more processor(s) 804 to perform operations, such as the operations for assessing input, as described with reference to FIG. 6 and/or FIG. 7.

The memory device(s) 806 can further store data 810 that can be accessed by the one or more processor(s) 804. For example, the data 810 can include any data used for assessing input, as described herein. The data 810 can include one or more table(s), function(s), algorithm(s), model(s), equation(s), etc. for assessing input according to example embodiments of the present disclosure.

The one or more computing device(s) 802 can also include a communication interface 812 used to communicate, for example, with the other components of system. The communication interface 812 can include any suitable components for interfacing with one or more network(s), including for example, transmitters, receivers, ports, controllers, antennas, or other suitable components.

Figure 9:
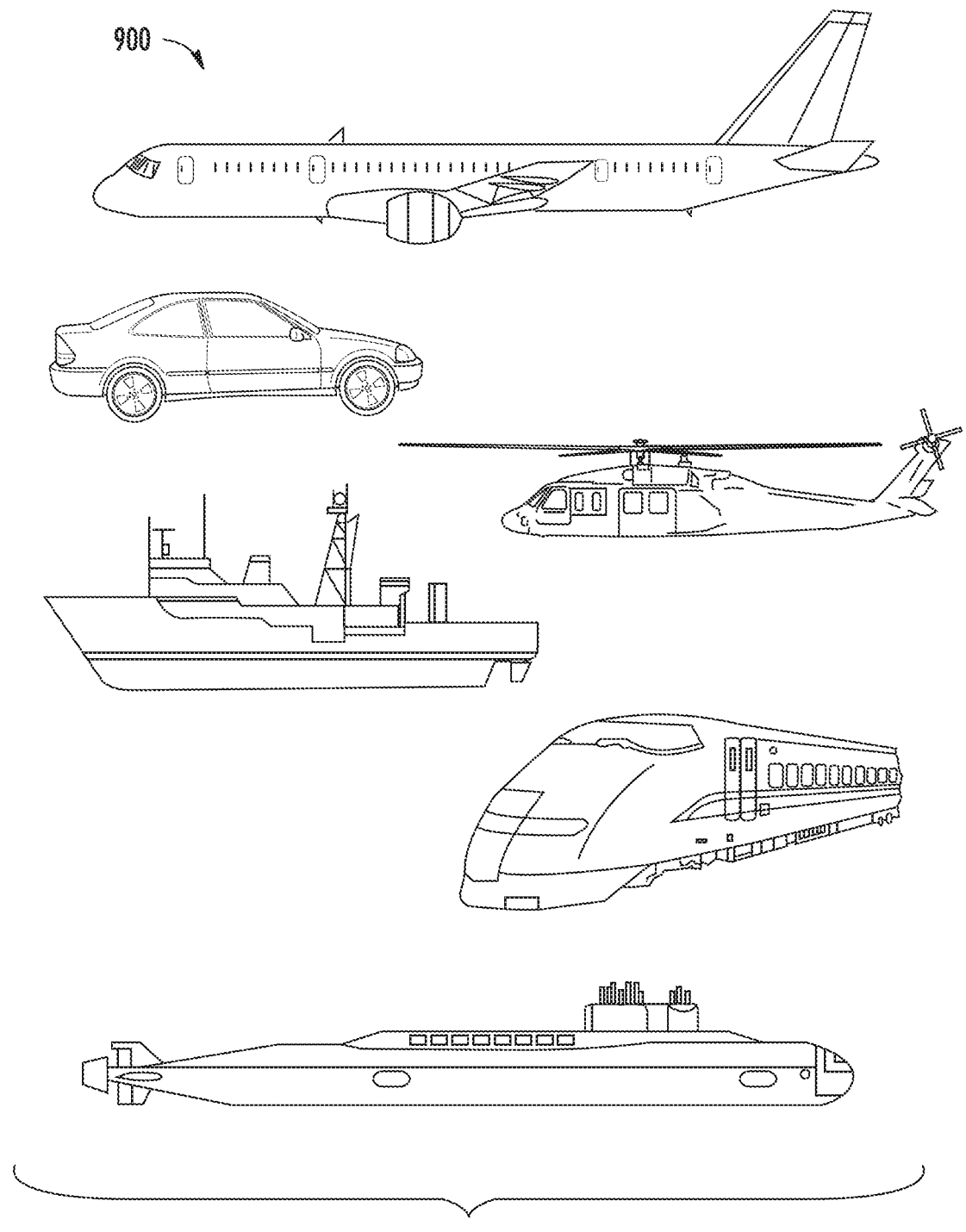
FIG. 9 depicts example vehicles according to example embodiments of the present disclosure.

Referring now to FIG. 9, example vehicles 900 according to example embodiments of the present disclosure are depicted. The systems and methods of the present disclosure can be implemented on an aerial vehicle, helicopter, automobile, boat, submarine, train, and/or any other suitable vehicles. While the present disclosure is described herein with reference to an aerial vehicle implementation, this is intended only to serve as an example and not to be limiting. One of ordinary skill in the art would understand that the systems and methods of the present disclosure can be implemented on other vehicles without deviating from the scope of the present disclosure.

The technology discussed herein makes reference to computer-based systems and actions taken by and information sent to and from computer-based systems. One of ordinary skill in the art will recognize that the inherent flexibility of computer-based systems allows for a great variety of possible configurations, combinations, and divisions of tasks and functionality between and among components. For instance, processes discussed herein can be implemented using a single computing device or multiple computing devices working in combination. Databases, memory, instructions, and applications can be implemented on a single system or distributed across multiple systems. Distributed components can operate sequentially or in parallel.

Although specific features of various embodiments may be shown in some drawings and not in others, this is for convenience only. In accordance with the principles of the present disclosure, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A system for assessing input from an operator, comprising:
 a memory device; and
 one or more processors configured to:
  determine a state of a vehicle;
  obtain data indicating an expected operator input based on the state of the vehicle;
  obtain data indicating an actual operator input;
  determine a state of operator behavior based on the expected operator input and the actual operator input;
  determine a control action for the vehicle based on the state of the vehicle and the state of operator behavior; and
  implement the control action,
 wherein the one or more processors define an operating envelope that is a set of rules based on the expected operator input under which the operator is permitted to operate,
 wherein the state of operator behavior is determined to be normal when the actual operator input is within the operating envelope, and is determined to be abnormal when the actual operator input is outside of the operating envelope,
 wherein the state of the vehicle is determined to be abnormal during a stalled state or an engine failure state, and is determined to be normal when not in the stalled state or the engine failure state,
 wherein when the state of the vehicle is determined to be the stalled state and the state of operator behavior is determined to be abnormal, the control action comprises:
  tightening the operating envelope by adding additional rules to the operating envelope, and
 wherein, when the state of the vehicle is determined to be the stalled state, the one or more processors ignore a signal indicating a backward movement of a yoke of the vehicle and operate the vehicle as if the yoke was moved to an expected position during the stalled state.

2. The system of claim 1, wherein when the state of the vehicle is determined to be abnormal and when the state of operator behavior is determined to be normal, the control action comprises broadening the operating envelope.

3. The system of claim 1, wherein when the state of the vehicle is determined to be normal and when the state of operator behavior is determined to be abnormal, the control action comprises tightening the operating envelope.

4. The system of claim 1, wherein determining the state of operator behavior based on the expected operator input and the actual operator input further comprises comparing an actual control polarity with an expected control polarity.

5. The system of claim 1, wherein determining the state of operator behavior based on the expected operator input and the actual operator input further comprises comparing an actual control selection with an expected control selection.

6. The system of claim 1, wherein determining the state of operator behavior based on the expected operator input and the actual operator input further comprises comparing an actual control decision with an expected control decision.

7. The system of claim 1, wherein determining the state of operator behavior based on the expected operator input and the actual operator input further comprises comparing an actual control timing with an expected control timing.

8. The system of claim 1, wherein determining the state of operator behavior based on the expected operator input and the actual operator input further comprises determining whether an expected control signal is present.

9. A method for assessing input from an operator, comprising:
  determining, by one or more computing devices, a state of a vehicle;
  obtaining, by the one or more computing devices, data indicating an expected operator input based on the state of the vehicle;
  obtaining, by the one or more computing devices, data indicating an actual operator input;
  determining, by the one or more computing devices, a state of operator behavior based on the expected operator input and the actual operator input;
  determining, by the one or more computing devices, a control action for the vehicle based on the state of the vehicle and the state of operator behavior, and
  implementing, by the one or more computing devices, the control action,
  wherein the one or more computing devices define an operating envelope that is a set of rules based on the expected operator input under which the operator is permitted to operate,
  wherein the state of operator behavior is determined to be normal when the actual operator input is within the operating envelope, and is determined to be abnormal when the actual operator input is outside of the operating envelope,
  wherein the state of the vehicle is determined to be abnormal during a stalled state or an engine failure state, and is determined to be normal when not in the stalled state or the engine failure state,
  wherein when the state of the vehicle is determined to be abnormal and when the state of operator behavior is determined to be normal, the control action comprises broadening the operating envelope, by removing one or more rules from the set of rules under which the operator is permitted to operate and forming a broadened envelope, and
  wherein the method further comprises operating, by the one or more computing devices, the vehicle according to the actual operator input when the actual operator input is within the broadened envelope.

10. The method of claim 9, wherein when the state of the vehicle is determined to be abnormal and when the state of operator behavior is determined to be abnormal, the control action comprises tightening the operating envelope.

11. The method of claim 9, wherein when the state of the vehicle is determined to be normal and when the state of operator behavior is determined to be abnormal, the control action comprises tightening the operating envelope.

12. The method of claim 9, wherein determining the state of operator behavior based on the expected operator input and the actual operator input further comprises comparing an actual control polarity with an expected control polarity.

13. The method of claim 9, wherein obtaining the data indicating the actual operator input comprises obtaining a passively observed input.

14. The method of claim 9, wherein obtaining the data indicating the actual operator input comprises obtaining data indicating a condition of the operator.

15. The method of claim 14, wherein the condition of the operator includes a physiological condition of the operator.

16. The method of claim 15, wherein the data indicating the physiological condition includes at least one of a heart rate of the operator and a blood pressure of the operator.

17. An aerial vehicle comprising:
  a memory device; and
  one or more processors configured to:
    determine a state of the aerial vehicle;
    obtain data indicating an expected operator input based on the state of the aerial vehicle;
    obtain data indicating an actual operator input from an operator;
    determine a state of operator behavior based on the expected operator input and the actual operator input;
    determine a control action for the aerial vehicle based on the state of the aerial vehicle and the state of operator behavior; and
    implement the control action,
  wherein the one or more processors define an operating envelope that is a set of rules based on the expected operator input under which the operator is permitted to operate,
  wherein the state of operator behavior is determined to be normal when the actual operator input is within the operating envelope, and is determined to be abnormal when the actual operator input is outside of the operating envelope,
  wherein when the state of the aerial vehicle is determined to be a stalled state and the state of operator behavior is determined to be abnormal, the control action comprises:
    tightening the operating envelope, by adding additional rules to the operating envelope, and
  wherein, when the state of the aerial vehicle is determined to be the stalled state, the one or more processors ignore a signal indicating a backward movement of a yoke of the aerial vehicle and operate the vehicle as if the yoke was moved to an expected position during the stalled state.

* * * * *